(12) United States Patent
Satoh et al.

(10) Patent No.: US 6,849,670 B2
(45) Date of Patent: Feb. 1, 2005

(54) PHOTO-CURABLE REPARATIVE MATERIAL FOR DENTAL USE

(75) Inventors: Takeshi Satoh, Yamaguchi-ken (JP); Masataka Himeno, Yamaguchi-ken (JP); Hideki Kazama, Yamaguchi-ken (JP)

(73) Assignee: Tokuyama Corporation, Yamaguchi (JP)

(*) Notice: Subject to any disclaimer, the term of this patent is extended or adjusted under 35 U.S.C. 154(b) by 381 days.

(21) Appl. No.: 10/088,347

(22) PCT Filed: Jul. 19, 2001

(86) PCT No.: PCT/JP01/06276

§ 371 (c)(1),
(2), (4) Date: Mar. 18, 2002

(87) PCT Pub. No.: WO02/05752

PCT Pub. Date: Jan. 24, 2002

(65) Prior Publication Data

US 2003/0162863 A1 Aug. 28, 2003

(30) Foreign Application Priority Data

Jul. 19, 2000 (JP) .......................................... 2000-219125
Jan. 17, 2001 (JP) ............................................. 2001-8449

(51) Int. Cl.$^7$ .............................. C08J 3/28; A61K 6/08; C08K 9/06
(52) U.S. Cl. ......................... 522/64; 523/113; 523/115; 523/212; 523/220
(58) Field of Search ........................... 522/64; 523/113, 523/115, 212, 220

(56) References Cited

U.S. PATENT DOCUMENTS 4,265,723 A * 5/1981 Hesse et al. .................. 522/16
5,856,374 A * 1/1999 Ono et al. .................. 523/116
6,034,152 A * 3/2000 Burger et al. ............... 523/116

FOREIGN PATENT DOCUMENTS

JP         2000-53519       2/2000

* cited by examiner

Primary Examiner—Tae H. Yoon
(74) Attorney, Agent, or Firm—Sherman & Shalloway (57) ABSTRACT

A photocurable dental restorative comprising (i) 100 parts by weight of a polymerizable monomer, (ii) 0.01 to 5 parts by weight of a photopolymerization initiator of acylphosphine oxide, and (iii) 200 to 1900 parts by weight of an inorganic filler, wherein the inorganic filler (iii) is a mixed filler of:

(A) irregular-shaped inorganic particles having an average particle size of not smaller than 0.1 $\mu$m but smaller than 1 $\mu$m;

(B) spherical inorganic particles having an average primary particle size of not smaller than 0.1 $\mu$m but not larger than 5 $\mu$m; and (C) fine inorganic particles having an average primary particle size of not larger than 0.1 $\mu$m;

which are so blended as to satisfy the following mass ratios ① to ③:

① $mA/(mB+mC)=0.2$ to $3$
② $mB/(mB+mC)=0.5$ to $0.99$
③ $mC/(mB+mC)=0.01$ to $0.5$ where mA, mB and mC are masses of the inorganic particles (A) to (C).

The restorative features excellent handling property, and makes it possible to obtain a cured product having a high fracture toughness and excellently glossy surface.

11 Claims, 3 Drawing Sheets

PHOTO-CURABLE REPARATIVE MATERIAL FOR DENTAL USE

TECHNICAL FIELD

The present invention relates to a photocurable dental restorative used for the composite resin, hard resin, inlay, unlay, crown and the like.

BACKGROUND ART

A photocurable dental restorative is a photocurable composite material comprising a polymerizable monomer, a photopolymerization initiator and a filler as chief components, is capable of imparting color tone which is the same as that of natural teeth, is easy to handle, and has been frequently used for restoring the treated teeth and has, in recent years, been used for restoring gum teeth which must bear high occlusive pressures.

As compared to natural teeth, however, the above restorative has a low mechanical strength. When, for example, the crown materials such as inlay, unlay and crown are formed of the above photocurable dental restorative to restore the teeth, the crown material is often broken when the occlusive pressure is high.

Namely, restoration of the gum teeth that bear high occlusive pressures must be accompanied by aesthetic appearance such as a small change in the color tone after restoration and excellent surface glossiness, as well as a mechanical strength large enough to withstand high occlusive pressures.

As a photocurable dental restorative featuring excellent aesthetic appearance and strength, there has heretofore been known the one highly densely blended with a mixture of an inorganic filler having a relatively large average particle size and a fine powdery inorganic filler. For example, Japanese Unexamined Patent Publication No. 26226/2000 discloses a photocurable dental composite restorative containing an inorganic filler, a polymerizable monomer and a bisacylphosphine oxide as a polymerization initiator. There has further been described that the inorganic filler is a mixture of 40 to 99% by weight of a nearly spherical inorganic particles having an average particle size in a range of not smaller than 0.1 $\mu$m but not larger than 1 $\mu$m and 60 to 1% by weight of inorganic fine particles having an average particle size of not larger than 0.1 $\mu$m, and further that the photocurable dental composite restorative features a high stability against environmental light, easy to handle and exhibits excellent mechanical strength, surface glossiness and anti-wear of opposing dentition (hereinafter, the above restorative is simply referred to as "conventional restorative I").

It can surely be said that the above conventional restorative I is excellent in both aesthetic appearance and strength, and exhibits sufficient degree of properties in restoring, for example, front teeth. However, though the cured product of the conventional restorative I exhibits a bending strength which is as high as 200 MPa or more, its fracture toughness (KIC) which is an important property related to the breakage of the restorative is about 2.3 MPa·m$^{1/2}$, which is not necessarily satisfactory for restoring gum teeth to which high occlusive forces are exerted.

In restoring the gum teeth, it can be considered to use a restorative which places more importance on the strength and fracture toughness than on the aesthetic appearance since the gum teeth are less visible than the front teeth, to use a material like the conventional restorative I having excellent aesthetic appearance for the portions exposed on the surfaces and use a photocurable dental composite restorative which places more importance on the mechanical strength than on the aesthetic appearance for the inside of the teeth.

As the photocurable dental composite restorative placing more importance on the mechanical strength than on the aesthetic appearance, there has been known the one which uses, as the filler, a mixture of irregular-shaped inorganic particles having particular particle sizes, an inorganic spherical filler having a relatively large average particle size and a fine powdery inorganic filler, the filler being highly densely blended. Concretely speaking, Japanese Unexamined Patent Publication (Kokai) No. 53519/2000 discloses a photocurable dental restorative containing a bisacylphosphine oxide as a polymerization initiator, wherein there is used, as an inorganic filler, a mixed filler comprising (a) irregular-shaped inorganic particles having an average particle size of from 1 to 9 $\mu$m but containing particles of a size of not smaller than 10 $\mu$m in an amount of not more than 3% by weight, (b) nearly spherical inorganic particles having an average particle size of not smaller than 0.1 $\mu$m but not larger than 5 $\mu$m, and (c) fine inorganic particles having an average particle size of from 0.01 to 0.1 $\mu$m, satisfying the following conditions:

$$ma/(mb+mc)=0.2 \text{ to } 3$$

$$mb/(mb+mc)=0.5 \text{ to } 0.99$$

and $$mc/(mb+mc)=0.01 \text{ to } 0.5$$

where ma to mc are masses of the inorganic particles (a) to (c).

The cured body formed from the photocurable dental restorative (hereinafter simply referred to as "conventional restorative II") disclosed in the prior art, exhibits surface glossiness and can be practicably used as a restorative for the gum teeth, offering bending strength and fracture toughness which are as high as 278 MPa and 3.2 MPa·mm$^{1/2}$, respectively, and further featuring a high stability against environmental light and good handling property like those of the conventional restorative I.

However, the surface glossiness of the conventional restorative II is below the aesthetic level of the conventional restorative I. In restoring, for example, the front teeth maintaining good aesthetic appearance (though this method involves cumbersome operation), therefore, a crown can be fabricated by using the conventional restorative I for the portion exposed on the surface and by using the conventional restorative II that places more importance on the mechanical strength than on the aesthetic appearance for the inside of the teeth. In the dental clinic, however, there occurs a case where the surface of the conventional restorative II is not all covered with the conventional restorative I or a case where the underground is exposed due to the grinding for fine adjustment. In such cases, there arouses a problem in that a distinct difference appears in the surface glossiness between the conventional restorative I and the conventional restorative II.

DISCLOSURE OF THE INVENTION

It is therefore an object of the present invention to improve the surface glossiness while maintaining excellent properties of the conventional restorative II and, particularly, good fracture toughness and handling property.

In order to solve the above-mentioned problem, the present inventors have conducted an extensive study concerning the mechanical properties and surface glossiness (aesthetic appearance) of the photocurable dental restorative. In dealing with the photocurable composition containing a filler of a composition like that of the above-mentioned mixed filler and using a photopolymerization catalyst such as camphorquinone that is usually used for the dental materials, the present inventors have discovered the fact that the strength and the fracture toughness decrease with a decrease in the average particle size of the irregular-shaped inorganic particles in the mixed filler whereas when the acylphosphine oxide is used as a photopolymerization catalyst, the above properties are not almost deteriorated and the surface glossiness is improved due to the use of irregular-shaped inorganic particles having a small average particle size, and have thus accomplished the invention.

That is, according to the present invention, there is provided a photocurable dental restorative comprising (i) 100 parts by weight of a polymerizable monomer, (ii) 0.01 to 5 parts by weight of a photopolymerization initiator of acylphosphine oxide, and (iii) 200 to 1900 parts by weight of an inorganic filler, wherein the inorganic filler (iii) is a mixed filler of:

(A) irregular-shaped inorganic particles having an average particle size of not smaller than 0.1 μm but smaller than 1 μm;

(B) spherical inorganic particles having an average primary particle size of not smaller than 0.1 μm but not larger than 5 μm; and (C) fine inorganic particles having an average primary particle size of not larger than 0.1 μm;

which are so blended as to satisfy the following mass ratios ① to ③:

① mA/(mB+mC)=0.2 to 3
② mB/(mB+mC)=0.5 to 0.99
③ mC/(mB+mC)=0.01 to 0.5 where mA, mB and mC are masses of the inorganic particles (A) to (C).

According to the present invention, there is further provided a method of producing a photocurable dental restorative by preparing an inorganic filler by mixing:

(A) irregular-shaped inorganic particles having an average particle size of not smaller than 0.1 μm but smaller than 1 μm;

(B) spherical inorganic particles having an average primary particle size of not smaller than 0.1 μm but not larger than 5 μm; and (C) fine inorganic particles having an average primary particle size of not larger than 0.1 μm;

so as to satisfy the following mass ratios ① to ③:

① mA/(mB+mC)=0.2 to 3
② mB/(mB+mC)=0.5 to 0.99
③ mC/(mB+mC)=0.01 to 0.5 where mA, mB and mC are masses of the inorganic particles (A) to (C), and by mixing 100 parts by weight of a polymerizable monomer, 0.01 to 5 parts by weight of a photopolymerization initiator of acylphosphine oxide, and 200 to 1900 parts by weight of the above inorganic filler.

BEST MODE FOR CARRYING OUT THE INVENTION

The photocurable dental restorative of the present invention contains (i) a polymerizable monomer, (ii) a particular photopolymerization initiator, and (iii) a particular inorganic filler (mixed filler).

(i) Polymerizable Monomer:

As the polymerizable monomer which is the component (i), there can be used, without any limitation, known polymerizable monomers that have generally been used for the photocurable dental restoratives. Preferred examples of the polymerizable monomers include (meth)acrylate monomers having an acryloyl group and/or methacryloyl group. Concrete examples of such polymerizable monomers may be the following monomers [i-1] to [i-4].

[i-1] Monofunctional Vinyl Monomers:

Methacrylates such as methyl methacrylate, ethyl methacrylate, isopropyl methacrylate, hydroxyethyl methacrylate, tetrahydrofurfuryl methacrylate, glycidyl methacrylate, and acrylates corresponding to these methacrylates;

acrylic acid, methacrylic acid, p-methacryloyloxybenzoic acid, N-2-hydroxy-3-methacryloyloxypropyl-N-phenylglycin, 4-methacryloyloxyethyltrimellitic acid, and anhydrides thereof, 6-methacryloyloxyhexamethylenemalonic acid, 10-methacryloyloxydecamethylenemalonic acid, 2-methacryloyloxyethyldihydrodiene phosphate, 10-methacryloyloxydecamethylenedihydrodiene phosphate, and 2-hydroxyethylhydrodienephenyl phosphonate.

[i-2] Bifunctional Vinyl Monomers:

(a) Those of the Aromatic Compounds:

2,2-Bis(methacryloyloxyphenyl)propane, 2,2-bis[4-(3-methacryloyloxy)-2-hydroxypropoxyphenyl]propane, 2,2-bis(4-methacryloyloxyphenyl)propane, 2,2-bis(4-methacryloyloxypolyethoxyphenyl)propane, 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2-(4-methacryloyloxyethoxyphenyl)-2-(4-methacryloyloxydiethoxyphenyl)propane, 2-(4-methacryloyloxydiethoxyphenyl)-2-(4-methacryloyloxyditriethoxyphenyl)propane, 2-(4-methacryloyloxydipropoxyphenyl)-2-(4-methacryloyloxytripropoxyphenyl)propane, 2,2-bis(4-methacryloyloxypropoxyphenyl)propane, 2,2-bis(4-methacryloyloxyisopropoxyphenyl)propane, and acrylates corresponding to these methacrylates; and diadduct obtained by the addition reaction at 2:1 of a vinyl monomer having a —OH group (e.g., methacrylate such as 2-hydroxyethyl methacrylate, 2-hydroxypropyl methacrylate or 3-chloro-2-hydroxypropyl methacrylate, or an acrylate corresponding to the methacrylate) and a diisocyanate compound having an aromatic group, such as diisocyanatemethyl benzene or 4,4'-diphenylmethane diisocyanate.

(b) Those of the Aliphatic Compounds:

Ethylene glycol dimethacrylate, diethylene glycol dimethacylate, triethylene glycol dimethacrylate, butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate, and acrylates corresponding to these methacrylates;

diadducts obtained by the addition reaction at 2:1 of a vinyl monomer having a —OH group (e.g., methacrylate such as 2-hydroxyethyl methacrylate, 2-hydroxypropyl methacrylate, 3-chloro-2-hydroxypropyl methacrylate or acrylate corresponding to the methacrylate) and a diisocyanate compound (e.g., hexamethylene diisocyanate, trimethylhexamethylene diisocynate, diisocynatemethylcyclohexane, isophorone diisocyanate, or methylenebis(4-cyclohexyl isocyanate)); and acrylic anhydride, methacrylic anhydride, 1,2-bis(3-methacryloyloxy-2-hydroxypropoxy)ethane, and di(2-methacryloyloxypropyl)phosphate.

[i-3] Trifunctional Vinyl Monomers:

Methacrylates such as trimethylolpropane trimethacrylate, trimethylolethane trimethacrylate, pentaerythritol trimethacrylate and trimethylolmethane trimetharylate, and acrylates corresponding to these methacrylates.

[i-4] Tetrafunctional Vinyl Monomers:

Pentaerythritol tetramethacrylate and pentaerythritol tetraacrylate; and adducts obtained by the addition reaction at 1:2 of a diisocyanate compound such as diisocyanate-methylbenzene, diisocyanatemethylcyclohexane, isophoronediisocyanate, hexamethylenediisocyanate, trimethylhexamethylenediisocyanate, methylenebis(4-cyclohexylisocyanate), 4,4-diphenylmethanediisocyanate or tolylene-2,4-diisocyanate with a glycidol dimethacrylate or a glycidol acrylate.

The above-mentioned various polymerizable monomers can be used in a single kind or being mixed together in two or more kinds. In the present invention, there is preferably used a polymerizable monomer obtained by mixing a bifunctional vinyl monomer of an aromatic compound and a bifunctional vinyl monomer of an aliphatic compound at a weight ratio of 90:10 to 40:60.

(ii) Photopolymerization Initiator:

In the photocurable dental restorative of the present invention, an acylphosphine oxide is used as the photopolymerization initiator which is the component (ii). There is no particular limitation on the acylphosphine oxide provided it works as a polymerization initiator upon being decomposed by the irradiation with light. The invention, however, uses a monoacylphosphine oxide represented by the following general formula (I) or a bisacylphosphine oxide represented by the following general formula (II), (I)

(II)

wherein each of $R_1$, $R_2$, $R_3$, $R_4$ and $R_5$ is any one of the groups selected from the group consisting of a hydrogen atom, a halogen atom, an alkyl group, an alkoxyl group, an alkylthio group, and a substituted or unsubstituted aryl group, and each of $R_6$ and $R_7$ is any one of the groups selected from the group consisting of a substituted or unsubstituted alkyl group, a substituted or unsubstituted alkenyl group, and a substituted or unsubstituted aryl groups. Concerning $R_1$ to $R_7$, it is desired that a substituent that may be introduced into a group such as the aryl group is at least the one selected from the group consisting of a halogen atom, an alkyl group and an alkoxy group. When the substituted group is an alkyl group or an alkoxy group, in particular, it is desired that the number of carbon atoms is from 1 to 3.

According to the present invention, the monoacylphosphine oxide represented by the above general formula (I) or the bisacylphosphine oxide represented by the above general formula (II) is used as the photopolymerization initiator, in order to increase the fracture toughness of the cured product formed of the restorative, to improve stability against environmental light and improve handling property of the restorative. Besides, what is important is that use of the acylphosphine oxide does not cause a drop in the mechanical properties such as strength and fracture toughness even when irregular-shaped inorganic particles having a small average particle size are used in the mixed filler. As a result, it is allowed to improve the surface glossiness.

In the above general formulas (I) and (II), a halogen atom denoted by $R_1$ to $R_5$ is preferably a fluorine atom, a chlorine atom or a bromine atom.

Though there is no particular limitation on the alkyl group denoted by $R_1$ to $R_5$, it is generally desired to use the one of a straight chain or a branched chain having 1 to 18 carbon atoms. Particularly preferred alkyl group may be a methyl group, an ethyl group, an n-propyl group, an iso-propyl group, an n-butyl group, a t-butyl group or an n-octyl group.

Though there is no particular limitation on the alkoxy group and alkylthio group denoted by $R_1$ to $R_5$, it is generally desired to use those containing an alkyl group having a straight chain or a branched chain with 1 to 18 carbon atoms. A particularly preferred alkoxy group may be a methoxy group, an ethoxy group or an n-butoxy group, and a particularly preferred alkylthio group may be a methylthio group, an ethylthio group or an n-propylthio group.

An aryl group denoted by $R_1$ to $R_5$, $R_6$ and $R_7$ may not have been substituted or may have been substituted by at least one group selected from the group consisting of a halogen atom, an alkyl group and an alkoxy group as described earlier. A particularly preferred aryl group may be a phenyl group, a tolyl group, a xylyl group, a naphthyl group, a methoxyphenyl group or a dichlorophenyl group.

An alkyl group and an alkenyl group denoted by $R_6$ and $R_7$ may not have been substituted or may have been substituted by a group described above, and there is no particular limitation on the number of carbon atoms thereof. Generally, however, it is desired to use the one of a straight chain or a branched chain having 1 to 18 carbon atoms. A preferred alkyl group denoted by $R_6$ and $R_7$ may be the one exemplified concerning $R_1$ to $R_5$. As the preferred alkenyl group, there can be exemplified aryl groups, 3-butenyl groups and 3-octadenyl groups.

As the monoacylphosphine oxide represented by the above-mentioned general formula (I) preferably used in the present invention, there can be exemplified:

2,4,6-trimethylbenzoyldiphenylphosphine oxide,
2,6-dimethoxybenzoyldiphenylphosphine oxide,
2,6-dichlorobenzoyldiphenylphosphine oxide,
2,3,5,6-tetramethylbenzoyldiphenylphosphine oxide,
benzoyldi-(2,6-dimethylphenyl)phosphine oxide,
2,4,6-trimethylbenzoyldi-(2,6-dimethylphenyl)phosphine oxide, and
2,6-dimethyl-3-phenylpropionyldiphenylphosphine oxide.

As the bisacylphosphine oxide represented by the above general formula (II) that is particularly preferably used, there can be exemplified:

bis-(2,6-dichlorobenzoyl)phenylphosphine oxide;
bis-(2,6-dichlorobenzoyl)-2,5-dimethylphenylphosphine oxide,
bis-(2,6-dichlorobenzoyl)-4-propylphenylphosphine oxide,
bis-(2,6-dichlorobenzoyl)-1-naphthylphosphine oxide,
bis-(2,6-dimethoxybenzoyl)phenylphosphine oxide,
bis-(2,6-dimethoxybenzoyl)-2,4,4-trimethylpentylphosphine oxide,
bis-(2,6-dimethoxybenzoyl)-2,5-dimethylphenylphosphine oxide,
bis-(2,4,6-trimethylbenzoyl)phenylphosphine oxide, and
bis-(2,4,6-trimethylbenzoyl)-2,4,6-trimethylpentylphosphine oxide.

The monoacylphosphine oxide represented by the above general formula (I) and the bisacylphosphine oxide represented by the above general formula (II) may be used in one kind or being mixed together in two or more kinds, respectively.

In the present invention, the acylphosphine oxide used as the photopolymerization initiator is used in an amount of from 0.01 to 5 parts by weight and, more preferably, from 0.1 to 5 parts by weight per 100 parts by weight of the polymerizable monomer (i). When the amount of addition is smaller than 0.01 part by weight, the polymerization does not proceed to a sufficient degree. When the amount of addition is not smaller than 5 parts by weight, the cured product exhibits decreased properties and, particularly, decreased light resistance and increased tint, which are not desirable.

In the present invention, further, it is allowable to use other polymerization initiators in combination so far as the acylphosphine oxide represented by the general formula (I) or (II) is used in amounts within the above-mentioned range. As such other polymerization initiators, there can be used known thermal polymerization initiators or other photopolymerization initiators without any limitation. Preferably, however, there can be used the following compounds.

That is, as the thermal polymerization initiator, there can be used peroxides such as benzoyl peroxide, p-chlorobenzoyl peroxide, tert-butyl peroxy-2-ethyl hexanoate, tert-butylperoxy dicarbonate, and diisopropylperoxy dicarbonate; azo compounds such as azobisisobutylonitrile; boron compounds such as tributylborane, partial oxide of tributylborane, sodium tetraphenyl borate, sodium tetrakis(p-fluorophenyl) borate, and triethanolamine salt of tetraphenylboric acid; barbituric acids such as 5-butylbarbituric acid and 1-benzyl-5-phenylbarbituric acid; and sulfinates such as sodium benzenesulfinates and sodium p-toluenesulfinates.

As the ultraviolet ray or visible ray polymerization initiator, further, there can be exemplified benzoinalkyl ethers such as benzoinmethyl ether, benzoin ethyl ether and benzoinisopropyl ether; benzyl ketals such as benzyldimethyl ketal and benzyldiethyl ketal; benzophenones such as benzophenone, 4,4'-dimethylbenzophenone, and 4-methacryloxybenzophenone; α-diketones such as diacetyl, 2,3-pentadion benzyl, camphorquinone, 9,10-phenanthraquinone and 9,10-anthraquinone; and thioxanthone derivatives such as 2,4-diethoxythioxanthone, 2-chlorothioxanthone and methylthioxanthone.

These other polymerization initiators are not only used in a single kind but can also be used in a combination of a plurality of kinds as required. Further, a preferred amount of addition thereof is from 0.01 to 5 parts by weight and, particularly, from 0.1 to 5 parts by weight per 100 parts by weight of the polymerizable monomer.

(iii) Inorganic Filler (Mixed Filler):

In the photocurable dental restorative of the present invention, it is important to use, as an inorganic filler which is the component (iii), a mixed filler of a blend of the irregular-shaped inorganic particles (A), the spherical inorganic particles (B) and the fine inorganic particles (C). Use of the mixed filler makes it possible to further improve the surface glossiness yet maintaining excellent mechanical properties equivalent to those of the above-mentioned conventional restorative II.

In the present invention, the spherical particles stand for those particles which appear in a round shape when observed in a unit visible field by taking a picture of the filler using a scanning electron microscope (hereinafter abbreviated as SEM), and have an average degree of symmetry of not smaller than 0.6 (which includes a true sphere), the average degree of symmetry being found by dividing the particle size in a direction at right angles with a maximum size thereof by the maximum size thereof.

Irregular-shaped Inorganic Particles (A):

The irregular-shaped inorganic particles (A) used in the present invention have an average particle size of not smaller than 0.1 µm but smaller than 1 µm and, preferably, not smaller than 0.5 µm but smaller than 1 µm. When there are used irregular-shaped inorganic particles having an average particle size of not smaller than 1 µm, the cured product of the dental restorative exhibits decreased surface glossiness. When there are used irregular-shaped inorganic particles having an average particle size of not larger than 0.1 µm, the cured product exhibits decreased mechanical properties, i.e., exhibits decreased strength and decreased fracture toughness.

The average particle size of the irregular-shaped inorganic particles stand for an average volume particle size ($D_{50}$) calculated from a particle size distribution as measured by a laser diffraction/scattering method (usually, the particles having particle sizes of not smaller than 1 µm are measured by the laser diffraction method, and particles having particle sizes of not larger than 1 µm are measured by the scattering method).

There is no particular limitation on the material (component) of the irregular-shaped inorganic particles (A) and any inorganic material can be used without any particular limitation provided it satisfies the above-mentioned conditions. Concretely, there can be used a borosilicate glass, a soda glass, a glass containing heavy metals (e.g., barium, strontium, zirconium), aluminosilicate, fluoroaluminosilicate, glass ceramics, silica as well as composite inorganic oxides such as silica-zirconia, silica-titania and silica-alumina.

The irregular-shaped inorganic particles (A) need not necessarily be those comprising a single kind of inorganic material so far as their average particle size lies within the above-mentioned range, but may comprise two or more kinds of mixed particles having different average particle sizes and of different materials (components). When the mixed particles comprising two or more kinds of irregular-shaped inorganic particles are used in the present invention, however, it is necessary that the mixed particles have an average particle size that lies within the above-mentioned range.

It is further desired that the particles included in the above irregular-shaped inorganic particles (A) have a minimum particle size of not smaller than 0.1 μm and, particularly, not smaller than 0.15 μm. The particles having particle sizes smaller than the above value may behave as fine inorganic particles (C) that will be described later.

Spherical Inorganic Particles (B):

The spherical inorganic particles (B) used in the present invention are round-shaped having an average degree of asymmetry of not smaller than 0.6 and, particularly, not smaller than 0.8 as described above, and have an average primary particle size of not smaller than 0.1 μm but not larger than 5 μm. When the particles are not round-shaped (average degree of symmetry is smaller than 0.6) or when the average particle size is greater than the above range, the cured product of the restorative exhibits poor luster (aesthetic appearance). When the average primary particle size is not larger than 0.1 μm, the inorganic particles become equivalent to the fine inorganic particles (C) that will be described later. Namely, this becomes equivalent to when no spherical inorganic particle (B) is used and, hence, the cured product exhibits poor luster. Besides, the inorganic filler is not highly densely filled resulting in a decrease in the mechanical strength and an increase in the thermal expansion. From the viewpoint of surface glossiness and abrasion resistance of the cured product, in particular, it is desired that the average primary particle size is not smaller than 0.1 μm but is not larger than 1 μm.

The average primary particle size of the spherical particles stands for an average size (arithmetic mean value) of the simple particles (independent particles) or of the primary particles constituting the aggregated particles as observed through the SEM photography.

In the present invention, the spherical inorganic particles (B) can be mixed to other inorganic particles (A), (B) in a form in which the individual particles are independently existing, or can be used in a state in which the independent particles are aggregated together as primary particles so as to exist as aggregates (the aggregate is the one in which the primary particles are bonded to one another to a degree to hold the shape of the primary particles, but does not include those in which the primary particles are coagulated together by a secondary force or in which portions of the surfaces of the primary particles are melt-adhered together, i.e., the primary particles are melt-adhered together to such a degree that the shapes of the primary particles cannot be recognized).

That is, since the primary particles are holding their shapes, use of the spherical inorganic particles (B) containing the aggregates of the primary particles does not impair the effect that stems from the shape (spherical shape of the primary particles. Further, when the spherical inorganic particles (B) including the aggregates are mixed with other inorganic particles or are kneaded with components other than the filler, the aggregates are disintegrated into sizes of not larger than 5 μm or into the state of primary particles, exhibiting the effect equivalent to that of when there are used the spherical inorganic particles (B) without including aggregates thereof.

It is therefore desired that the spherical inorganic particles (B) have an average particle size as measured in a form including the aggregates thereof (measured by the laser diffraction/scattering method) in a range of from 0.1 to 50 μm and, particularly, from 0.1 to 20 μm as far as the primary particles have a spherical shape and the average primary particle size lies within the above-mentioned range. When the average particle size is not smaller than the above-mentioned range, it becomes difficult to disintegrate the aggregates and, hence, to homogeneously knead them together with the above-mentioned irregular-shaped inorganic particles (A). Therefore, the cured product of the restorative may lose the mechanical strength. Further, the cured product may lose the luster. In the particle size distribution of the primary particles, further, it is desired that the coefficient of change in the particle size is not larger than 0.3. The coefficient of change in the primary particle size can be calculated from the image obtained by the above-mentioned SEM observation. Use of the spherical inorganic particles (B) having excellent monodispersion property makes it possible to improve the handling property of the photocurable dental restorative.

Further, since the aggregates can be easily disintegrated into sizes of smaller than 5 μm, it is desired that a maximum size of the aggregates of the spherical inorganic particles (B) is not larger than 100 μm and, more preferably, not larger than 20 μm. A maximum size of the aggregates is found by dispersing an aqueous mixture containing 20% by weight of the inorganic particles using ultrasonic waves for one hour and by measuring the distribution of particle sizes, as demonstrated by Examples appearing later.

Though there is no particular limitation on the material of the spherical inorganic particles (B), there is generally used an inorganic oxide such as amorphous silica, silica-zirconia, silica-titania, silica-titania-barium oxide, quartz or alumina. These inorganic oxides can be used as the spherical inorganic particles (B) in the form of a composite oxide being added with a small amount of an oxide of a metal of the Group I of periodic table from the standpoint of obtaining a dense product through the firing at a high temperature. According to the present invention, a composite oxide containing silica and zirconia as chief constituent components is particularly preferably used as the spherical inorganic particles (B) since it exhibits X-ray contrast property and makes it possible to obtain a cured product exhibiting excellent abrasion resistance.

Further, the spherical inorganic particles (B) need not necessarily be of a single kind of component as far as the shape thereof and the average primary particle size thereof satisfy the above-mentioned conditions, but may be a mixture of particles having different average particle sizes and of different materials as disclosed in, for example, Japanese Examined Patent Publication (Kokoku) No. 10603/1991.

There is no particular limitation on the method of producing the spherical inorganic particles (B) comprising the above-mentioned inorganic oxide or the composite oxide. Industrially, however, they are generally prepared by the hydrolysis of a metal alkoxide. According to this method, monodispersed particles of spherical inorganic particles having an average degree of asymmetry of not smaller than 0.6 can be produced in a solution. In order to maintain surface stability of the spherical inorganic particles (B), further, it is desired to decrease the silanol groups on the surface. For this purpose, there is often preferably employed means of firing at a temperature of from 500 to 1000° C. When this processing is conducted, the particles aggregate during the drying and firing. It is therefore desired to disintegrate the aggregated particles by using a jet mill, a vibration ball mill or a nanomizer and to adjust the particle size such that the average particle size of the particles in the form of including the aggregates thereof and the maximum size of the aggregates thereof lie within the above-mentioned ranges.

In the above-mentioned spherical inorganic particles (B), further, it is desired that a minimum particle size is not smaller than 0.1 μm and, particularly, not smaller than 0.15 μm. Namely, particles of a size smaller than the above value may behave as the fine inorganic particles (C) described below.

(C) Fine Inorganic Particles:

The fine inorganic particles (C) used in the present invention has an average primary particle size of not larger than 0.1 μm, preferably, from 0.01 to 0.1 μm and, more preferably, from 0.05 to 0.09 μm. The fine inorganic particles (C) are to fill the gaps among the irregular-shaped inorganic particles (A) and the spherical inorganic particles (B). Use of the fine inorganic particles (C) enables the filler to be densely filled in the photocurable dental restorative and, hence, makes it easy to obtain a cured product of the restorative having a large mechanical strength and a small coefficient of thermal expansion. When, for example, the average primary particle size is larger than the above-mentioned range (in such a case, the inorganic particles become equivalent to the irregular-shaped inorganic particles (A), to the spherical inorganic particles (B) or to none of them depending upon their particle shapes and particle sizes), it becomes difficult to densely fill the filler, whereby the cured product exhibits insufficient mechanical properties or surface glossiness and, besides, exhibits decreased aesthetic appearance (luster) when the inorganic particles are irregular-shaped.

There is no particular limitation on the shape of the fine inorganic particles (C) so far as their average primary particle size lies within the above-mentioned range; i.e., the fine inorganic particles (C) may assume any shape such as spherical shape, needle-like shape, plate-like shape or irregular-shaped shape. From the standpoint of the strength and surface glossiness (luster) of the cured product, however, it is desired to use the spherical particles having an average degree of symmetry of not smaller than 0.6.

The fine inorganic particles (C), too, can be used in a form of including aggregates thereof like the above-mentioned spherical inorganic particles (B). To highly densely fill the filler by filling the gaps among the irregular-shaped inorganic particles (A) and the spherical inorganic particles (B), however, it is desired that the fine inorganic particles (C) have an average particle size of from 0.01 to 50 μm and, particularly, from 0.01 to 20 μm as measured in a form including the aggregates therein. Further, since the aggregates can be easily disintegrated, it is desired that the maximum size of the aggregate is not larger than 100 μm and, particularly, not larger than 20 μm as measured by the above-mentioned method.

The average primary particle size of the fine inorganic particles (C), the maximum size of the aggregates thereof and the average particle size of the particles inclusive of the aggregates thereof, can be measured by the methods described below.

That is, the average primary particle size is obtained by measuring the sizes of the individual particles by the SEM observation and by finding an average value thereof. When the fine inorganic particles (C) are irregular-shaped and it is difficult to find the average size thereof by the SEM observation, the size of the primary particle having the greatest size is, first, found by the SEM observation. Then, the aggregated particles are separated by using a filter having a size of passage of about 2 to 5 times as large as the size of the largest primary particle (usually, about 1 μm), and the particles that have passed through the filter are measured by a light scattering method (laser scattering method, dynamic light scattering method, white light deflection method) to find an average primary particle size.

The maximum size of the aggregates can be measured by the above-mentioned laser diffraction/scattering method. The average particle size of the particles including the aggregates thereof can be measured by using a measuring instrument based on the laser diffraction/scattering method (e.g., LS230 manufactured by Beckman Coultar Co.) which is capable of measuring even the particle sizes of not larger than 0.1 μm.

Though there is no particular limitation on the material of the fine inorganic particles (C), there are favorably used the same materials as those of the above-mentioned spherical inorganic particles (B), i.e., such inorganic oxides as ultrafine powdery silica, ultrafine alumina, ultrafine zirconia, ultrafine titania, amorphous silica, silica-zirconia, silica-titania, silica-titania-barium oxide, quartz and alumina. Further, since dense particles are easily formed through the firing at a high temperature, it is allowable to obtain a composite oxide obtained by adding a small amount of an oxide of a metal of the Group I of periodic table to the above-mentioned inorganic oxide.

The fine inorganic particles (C) need not necessarily be comprised of a single kind of component as far as the average primary particle size lies within the above-mentioned range, but may be a mixture of a plurality of kinds of particles having different average primary particle sizes and of different materials.

On a particle size distribution (volume frequency) curve of the fine inorganic particles (C) measured by the above-mentioned method, it is desired that peaks representing the distributions of the independent particles which are not aggregated and of the aggregated particles having an aggregated particle size of not larger than 0.2 μm (hereinafter referred to as fine aggregated particles) (these peaks are usually not separable and are observed as a single peak), are not substantially overlapped on the peaks of the particle size distributions of the irregular-shaped inorganic particles (A) and of the spherical inorganic particles (B). It is desired that a maximum size (observed by SEM) of an independent particle that is not aggregated is not larger than 0.15 μm and, more preferably, not larger than 0.1 μm. Even when the peaks representing the distributions of the independent particles and of the fine aggregated particles of the fine inorganic particles (C) are overlapped on the irregular-shaped inorganic particles (A) and on the spherical inorganic particles (B), it is desired that the peak areas of the overlapped portions are not larger than 10% by volume. That is, when there exist fine inorganic particles (C) having such particle sizes in large amounts, it becomes difficult to adjust various properties by adjusting the mass ratios of the inorganic particles (A) to (C), which will be described below.

Preparation of the Mixed Filler (iii):

A mixed filler which is the component (iii) used in the present invention is obtained by mixing the above-mentioned irregular-shaped inorganic particles (A), spherical inorganic particles (B) and fine inorganic particles (C) so as to satisfy the following mass ratios ① to ②:

① mA/(mB+mC)=0.2 to 3

② mB/(mB+mC)=0.5 to 0.99

③ mC/(mB+mC)=0.01 to 0.5 where mA, mB and mC are masses of the inorganic particles (A) to (C).

That is, when the amount of the irregular-shaped inorganic particles (A) in the mixed filler (iii) is smaller than the above-mentioned range, it becomes difficult to obtain a cured product having a large fracture toughness. When its amount is larger than the above-mentioned range, the cured product of the restorative exhibits decreased luster (aesthetic appearance).

When the amount of the spherical inorganic particles (B) in the mixed filler is larger than the above-mentioned range (i.e., when the amount of the fine inorganic particles (C) is small), the cured product of the restorative exhibits a decreased mechanical strength. When its amount is small (when the amount of the fine inorganic particles (C) is large), on the other hand, the cured product exhibits not only a decreased mechanical strength but also a decreased luster (aesthetic appearance).

Further, when the amount of the irregular-shaped inorganic particles (A) or of the fine inorganic particles (C) in the mixed filler is larger than the above-mentioned range, it becomes difficult to highly densely fill the filler in the polymerizable monomer, whereby the mechanical strength decreases and the paste-handling property decreases, too.

In the present invention, it is most desired to so blend the inorganic particles (A) to (C) as to satisfy the following mass ratios ①' to ③';

①' mA/(mB+mC)=0.4 to 2.3

②' mB/(mB+mC)=0.6 to 0.9

③' mC/(mB+mC)=0.1 to 0.4 from the standpoint of mechanical strength, fracture toughness and paste-handling property.

In mixing the above-mentioned inorganic particles (A) to (C), the fine inorganic particles (C) tend to be easily aggregated, and are used for filling the gaps among the irregular-shaped inorganic particles (A) and the spherical inorganic particles (B). Preferably, therefore, the spherical inorganic particles (B) and the fine inorganic particles (C) are mixed together and, then, the irregular-shaped inorganic particles (A) are mixed.

It is desired that the mixed filler which is the component (iii) obtained as described above has its surfaces treated to be hydrophobic in order to improve dispersion in the polymerizable monomer which is the component (i). There is no particular limitation on treating the surfaces to be hydrophobic, and a known method can be employed without limitation. Representative examples of the method of treating the surfaces include a method of using a silane coupling agent or a titanate coupling agent for imparting hydrophobic property, and a method of graft-polymerizing the surfaces of the particles with the polymerizable monomer. Such a surface treatment may be executed after the inorganic particles (A) to (C) have been mixed together, or may be executed for each of the inorganic particles (A) to (C).

In the present invention, it is desired that the surfaces of the irregular-shaped inorganic particles (A) are treated with a silane coupling agent represented by the following general formula (III):

wherein $R_8$ is a hydrogen atom or a methyl group, $R_9$ is an alkoxy group, a chlorine atom or an isocyanate group, $R_{10}$ is an alkyl group having 1 to 6 carbon atoms, m is an integer of 2 to 3, and n is an integer of 8 to 20.

Upon treating the surfaces of the irregular-shaped inorganic particles (A) with the silane coupling agent, affinity is greatly improved between the inorganic particles (A) and the polymerizable monomer, enabling the mixed filler to be highly densely filled. Therefore, the cured product offers great advantage such as a decreased coefficient of thermal expansion and improved abrasion resistance enabling the restorative to exhibit improved durability in the oral cavity.

As the silane coupling agents represented by the general formula (III), there can be exemplified 10-methacryloyloxydecyltrimethoxysilane, 10-methacryloyloxydecylmethyldimethoxysilane, 10-methacryloyloxydecyltrichlorosilane and 8-methacryloyloxyoctyltrimethoxysilane. These silane coupling agents can be used alone or being mixed together in two or more kinds. Or, they may be used in combination with other surface treating agents such as γ-methacryloyloxypropyltrimethoxysilane and hexamethyldisilazane within a range in which their effects are not hindered.

The fine inorganic particles (C) can be treated for their surfaces with a silane coupling agent represented by the following general formula (IV), wherein $R_{11}$ is a hydrogen atom or a methyl group, $R_{12}$ is an alkoxy group, a chlorine atom or an isocyanate group, $R_{13}$ is an alkyl group having 1 to 6 carbon atoms, m is an integer of 2 to 3, and n is an integer of 2 to 3.

The silane coupling agent has the structure same as that of the silane coupling agent expressed by the above-mentioned general formula (III) except that the alkylene group is short (n=2 to 3). That is, when there are used fine inorganic particles (C) of which the surfaces are treated with a silane coupling agent having a long alkylene group (n=8 to 20) as represented by the general formula (III), the restorative paste acquires thixotropic property and impairs the pasting operation such as permitting the viscosity to change during the pasting operation and forming yarns, making it difficult to carry out the modeling operation. However, use of the silane coupling agent having a short alkylene group (n=2 to 3) represented by the general formula (IV) makes it possible to effectively prevent such inconveniences.

A representative example of the silane coupling agent expressed by the general formula (IV) may be a γ-methacryloyloxypropyltrimethoxysilane.

The surfaces of the spherical inorganic particles (B) can be treated by using the silane coupling agent of either the general formula (III) or the general formula (IV). When the spherical inorganic particles (B) only are to be treated for their surfaces, it is desired to use the silane coupling agent of the above general formula (III). As will be described later, however, it is desired that the spherical inorganic particles (B) are treated for their surfaces after being mixed with the spherical inorganic particles (C). In this case, it is desired to treat the surfaces with the silane coupling agent of the general formula (IV).

There is no particular limitation on the method of treating the surfaces of the inorganic particles (A) to (C) with the above-mentioned silane coupling agent, and a conventional method can be employed. For example, the inorganic particles which are to be treated for their surfaces and the silane coupling agent are dispersed and mixed in a suitable solvent by using a ball mill or the like, are dried by using an evaporator or a spray-drier, and are heated at 50 to 150° C. so as to treat the surfaces. Further, the inorganic particles which are to be treated for their surfaces and the silane coupling agent are heated with stirring in a solvent such as alcohol to treat the surfaces. The fine inorganic particles (C) have a strong cohesive force. When treated alone, therefore, the surfaces of the fine inorganic particles (C) are not likely to be treated to be hydrophobic. It is therefore desired to mix the fine inorganic particles (C) with the whole or part of the spherical inorganic particles (B) and treat the mixed particles for their surfaces with the silane coupling agent by the above-mentioned method. Prior to treating the surfaces with the silane coupling agent, the spherical inorganic particles (B) and the fine inorganic particles (C) are mixed together, whereby aggregation of the fine inorganic particles (C) is disintegrated and the surfaces are treated more efficiently. In this case, it is desired to use the silane coupling agent of the above general formula (IV).

In the surface treatment by using the silane coupling agent of the general formula (III) or (IV), there is no particular limitation on the amount of the silane coupling agent. From the standpoint of the paste-handing property and properties of the cured product, however, it is desired that the amount of its use is from 1 to 10 parts by weight per 100 by weight of the inorganic particles that are to be treated for their surfaces.

It is further desired that the mixed filler of the component (iii) obtained by mixing the irregular-shaped inorganic particles (A), spherical inorganic particles (B) and fine inorganic particles (C) as described above, is highly dispersible in the polymerizable monomer which is the component (i) from the standpoint of favorably handing the restorative, obtaining the cured product having an increased strength and enhancing the aesthetic appearance (luster) of the obtained cured product. For this purpose, it is desired that the particle size of the mixed filler has been so adjusted that when it is mixed with the polymerizable monomer (i) and other components to prepare a restorative paste, the aggregates of the spherical inorganic particles (B) and of the fine inorganic particles (C) have maximum sizes of not larger than 20 $\mu$m and, preferably, not larger than 10 $\mu$m, and the total amount of the aggregate is not larger than 20% by volume of the whole amount of the mixed filler. Most desirably, further, the particle size distribution (volume frequency) curve of the mixed filler in the state of a paste has at least one peak (peak of the fine inorganic particles (C)) at a position of a particle size of not larger than 0.1 $\mu$m, has at least one peak (peak of the irregular-shaped inorganic particles (A) and of the spherical inorganic particles) at a position of a particle size which is not smaller than 0.1 $\mu$m but is not larger than 1 $\mu$m, and has no peak (that stems from the aggregate) at a position of the particle size which is not smaller than 5 $\mu$m.

The particle size distribution of the mixed filler (iii) in the state of a paste can be found by dissolving the paste in a solvent such as ethanol capable of dissolving the polymerizable monomer (i) so that it is diluted, and measuring the particle size distribution by using the diluted solution. In this case, it is desired to take a measurement by using an apparatus (e.g., LS230 manufactured by Beckman Coulter Co.) which is capable of measuring particles smaller than 0.1 $\mu$m up to particles larger than 10 $\mu$m simultaneously without the need of separately using apparatuses depending upon the particle sizes.

The dispersibility of the mixed filler (iii) in the polymerizable monomer (i) can be evaluated in terms of a volume of pores due to strongly aggregated particles having pore sizes of not smaller than 0.08 $\mu$m in the filler as disclosed in Japanese Unexamined Patent Publication (Kokai) No. 12305/1996.

Here, the pore size and the volume of the micro pores due to strongly aggregated particles are measured by the mercury porosimetry, the pore size being determined from the pore distribution found by the measurement of the porous volume while applying the pressure, and the volume of the micro pores due to strongly aggregated particles of each size being found based on a porous volume curve measured while reducing the pressure by taking into consideration the pore size measured while reducing the pressure and a shift in the pore size measured while applying the pressure.

Namely, the dispersibility of the mixed filler (iii) in the polymerizable monomer (i) increases with a decrease in the volume of the micro pores due to strongly aggregated particles of a pore size of not smaller than 0.08 $\mu$m as measured by the above-mentioned method. It is desired that the volume of the micro pores due to strongly aggregated particles of the mixed filler (iii) used in the present invention is not larger than 0.1 cc/g of filler. By using the mixed filler (iii) having a volume of the micro pores due to strongly aggregated particles adjusted to lie in the above-mentioned range, it is allowed to obtain a photocurable dental restorative capable of forming a cured product having a particularly large mechanical strength.

The mixed filler (iii) having the above-mentioned particle size distribution and having a volume of the micro pores due to strongly aggregated particles adjusted to lie in the above-mentioned range, is obtained by, for example, dispersing the inorganic particles (A) to (C) (particularly, inorganic particles (B) and (C) that tend to be easily aggregated) in a medium such as pure water under high treating pressure such as 10 to 100 MPa by using an emulsifying/dispersing nanomizer of the type of giving a shock under super-high pressure. Usually, the dispersion requires a longer time with a decrease in the treating pressure. It is therefore desired that the treating pressure is from 50 to 70 MPa.

In the photocurable dental restorative of the present invention, the mixed filler (iii) prepared as described above is blended in an amount of from 200 to 1900 parts by weight and, preferably, from 300 to 900 parts by weight per 100 parts by weight of the polymerizable monomer which is the component (i). When the blended amount of the mixed filler (iii) is smaller than 200 parts by weight, it becomes difficult to obtain a cured product having a large mechanical strength. When the blended amount exceeds 1900 parts by weight, it becomes difficult to homogeneously disperse the mixed filler (iii) in the polymerizable monomer (i), and the paste of the photocurable dental restorative can be handled less easily.

Other Components to be Blended:

The photocurable dental restorative of the present invention can be blended with an amine compound in addition to the above-mentioned components (i) to (iii). Upon being blended with the amine compound, the cured product of the restorative exhibits further increased strength, and the unpolymerized amount in the surface can be decreased at the time of curing.

Examples of the amine compound include primary amines such as n-butylamine, n-hexylamine, n-octylamine and aniline; secondary amines such as N-methylaniline, N-methyl-p-toluidine, dibutylamine and diphenylamine; aliphatic tertiary amines such as triethylamine, tributylamine, N,N'-dimethylaniline, N,N'-dibenzylaniline and N,N'-dimethylaminoethyl methacrylate; and aromatic tertiary amines such as p-dimethylaminobenzoic acid, amyl p-dimethylaminobenzoate, ethyl p-dimethylaminobenzoate, N,N'-dimethylanthranic acid methyl ester, p-dimethylaminophenetyl alcohol, N,N'-di(β-hydroxyethyl)-p-toluidine, N,N'-dimethyl-p-toluidine and N,N'-diethyl-p-toluidine. Among them, it is most desired to use the aromatic tertiary amine.

The amine compounds may be used in one kind or being mixed in two or more kinds together, and the blending amount thereof is from 0.01 to 5 parts by weight and, particularly, from 0.1 to 5 parts by weight per 100 parts by weight of the polymerizable monomer which is the component (i).

The photocurable dental restorative of the present invention may be further blended with known additives in a range in which they do not impair the effect. As the additives, there can be exemplified a polymerization inhibitor, an antioxidant, a pigment and an ultraviolet ray absorber.

Preparation of the Photocurable Dental Restorative, Molding Thereof and Curing Thereof:

To use the photocurable dental restorative of the present invention, in general, the above-mentioned essential components (i) to (iii) and, as required, arbitrary components are taken up in predetermined amounts and are mixed together, defoamed in vacuum, and a paste of the photocurable dental restorative is once formed. Thereafter, the paste is molded into the form of a tooth and is cured.

Generally, the paste is molded and cured by (1) a method in which a cavity of a tooth to be restored is directly filled with the paste which is, then, molded into the shape of a tooth and is irradiated with intense light from a dedicated light irradiation device so as to be cured by polymerization, or by (2) a method in which the paste is heaped up on a support model or on a metal frame outside the oral cavity, molded into the shape of a tooth, cured by polymerization and is, then, mounted in the oral cavity by using a dental adhesive or the like to restore the tooth.

The source of light for curing, preferably, emits light of a wavelength which is effective in photo-decomposing the acylphosphine oxide (ii) which is a photopolymerization initiator, i.e., emits light of a wavelength in a range of from 250 to 500 nm. The lamp preferably used as a source of light will be a high-pressure mercury lamp, a low-pressure mercury lamp, a metal halide lamp, a photochemical fluorescent lamp, a xenon lamp or a halogen lamp. The irradiation time varies depending upon the brightness of the lamp and the distance of irradiation. Here, the brightness of the lamp and the distance of irradiation may be so set that the irradiation time (one second to 10 minutes) which is usually accepted in this field of work will suffice for the need.

The cured product which is cured by the irradiation with light can be used as a restorative in its own form. Through the heating, however, the cured product exhibits a further increased mechanical strength and becomes particularly suited as a tooth material. The effective heating temperature is from 80 to 120° C., and it is desired to conduct the heating for not shorter than one minute. The heating is effected after the curing by the irradiation with light; i.e., the paste that is heaped up does not flow, and the shape of the tooth is not collapsed.

EXAMPLES

The invention will now be concretely described by way of Examples to which only, however, the invention is in no way Limited.

The polymerizable monomers (i), photopolymerization initiators (ii) and amine compounds used in the following Examples and Comparative Examples are as described below.

| Polymerizable monomers (i) | |
|---|---|
| D-2.6E: | Bismethacryloylethoxyphenylpropane |
| 3G: | Triethylene glycol dimethacrylate |
| UDMA: | 1,6-Bis(methacrylethyloxycarbonylamino)-2,2,-4-trimethylhexane |
| Photopolymerization initiators (ii) | |
| BAPO: | Bis(2,4,6-trimethylbenzoyl)-phenylphosphine oxide |
| TPO: | 2,4,6-Trimethylbenzoyldiphenylphosphine oxide |
| CQ: | Camphorquinone (note: this is not the acylphosphine oxide of the invention) |
| Amine compound | |
| DMBE: | Ethyl p-dimethylaminobenzoate |

In Examples and Comparative Examples, further, the irregular-shaped inorganic particles (A), spherical inorganic particles (B) and fine inorganic particles (C) used for preparing the mixed filler (iii) are as described below.

| Irregular-shaped inorganic particles (A) | |
|---|---|
| A-1: | Irregular-shaped silica-zirconia (treated for the surfaces with a γ-methacryloxypropyltrimethoxysilane) average particle size, 0.8 μm |
| A-2: | Irregular-shaped silica-zirconia (treated for the surfaces with a 10-methacryloxydecyltrimethoxysilane) average particle size, 0.8 μm |
| A'-1: | Irregular-shaped silica-zirconia (treated for the surfaces with a γ-methacryloxypropyltrimethoxysilane) average particle size, 3.4 μm |
| (Note: falls outside the scope of the invention) | |
| Spherical inorganic particles (B) | |
| B-1: | Spherical silica-zirconia Average primary particle size, 0.52 μm Coefficient of change in the particle size, 0.14 Max. size of aggregated particles, 5.2 μm |
| B-2: | Spherical silica Average primary particle size, 0.62 μm Coefficient of change in the particle size, 0.06 Max. size of aggregated particles, 12 μm |
| B-3: | Spherical silica-titania (treated for the surfaces with a 10-methacryloxydecyltrimethoxysilane) Average primary particle size, 0.3 μm Coefficient of change in the particle size, 0.09 Max. size of aggregated particles, 6 μm |

-continued

| Fine inorganic particles (C) | |
|---|---|
| C-1: | Spherical silica-titania<br>Average primary particle size, 0.08 μm<br>Max. size of aggregated particles, 18 μm |
| C-2: | Spherical silica-zirconia<br>Average primary particle size, 0.06 μm<br>Max. size of aggregated particles, 18 μm |
| C-3: | Irregular-shaped silica (Reolosil QS102)<br>manufactured by Tokuyama Co.)<br>Average primary particle size, 0.015 μm |

The average particle size of the irregular-shaped inorganic particles (A) is found by dispersing an aqueous dispersion of 20% by weight thereof by ultrasonic waves for 20 minutes and by measuring the particle sizes by using a particle size distribution measuring instrument (Mastersizer manufactured by Malbern Co.) based on the laser diffraction/scattering method.

Concerning various inorganic particles used as the spherical inorganic particles (B) and the fine inorganic particles (C), the average primary particle size is that of forty independent particles (or primary particles constituting the aggregate) arbitrarily picked up by the SEM observation, and a maximum size of the aggregated particles is found by dispersing an aqueous dispersion of 20% by weight of inorganic particles by ultrasonic waves for one hour and by measuring the particle sizes by using a particle size distribution measuring instrument (Mastersizer manufactured by Malbern Co.) based on the laser diffraction/scattering method.

Concerning the inorganic particles of B-1, B-2 and B-3 used as the spherical inorganic particles (B), the primary particles are all round-shaped as observed using the SEM, and it is confirmed that the average degree of symmetry obtained by dividing the particle size in a direction at right angles with a maximum size by the maximum size is from 0.90 to 0.99.

In the following Examples and Comparative Examples, further, the mixed filler (iii) is measured for its volume of the micro pores due to strongly aggregated particles, preparation of the photocurable dental restorative, stability of the restorative against environmental light, handling property of the paste thereof, mechanical properties (bending strength, fracture toughness) of the cured product thereof, surface glossiness (luster), coefficient of thermal expansion and unpolymerized amount in the surface, in compliance with the methods described below.

(1) Volume of the Micro Pores Due to Strongly Aggregated Particles:

About 0.2 g of the filler dried to a sufficient degree was picked up and was measured for its pore sizes and porous distributions under a pressurized condition and under a reduced pressure condition by using a mercury porosimetry porous distribution measuring apparatus (Porosimeter 2000 manufactured by Carlo Erba Co.). From these results, the pore sizes and porous distributions were measured in compliance with the method disclosed in Japanese Unexamined Patent Publication (Kokai) No. 12305/1996 to find the volume of the micro pores due to strongly aggregated particles having pore sizes of not smaller than 0.08 μm (hereinafter simply referred to as volume of the micro pores due to strongly aggregated particles).

(2) Preparation of the Photocurable Dental Restorative:

Into an agate mortar, there were introduced a mixed filler (iii) of a predetermined amount and a solution of a polymerizable monomer obtained by adding a predetermined amount of the photopolymerization initiator (ii) to the polymerizable monomer (i) and homogeneously dissolving them in a dark place, which were then kneaded in the dark place to a sufficient degree, followed by defoaming in vacuum to obtain a paste-like homogeneous curable composition.

(3) Stability Against Environmental Light:

The distance between the source of light and the sample was so set that the intensity of illumination was 10,000 luxes on the surface of the paste-like sample of curable composition. A source of light was a 15-watt fluorescent lamp (trade name: Palook, manufactured by Matsushita Electric Industrial Co.), and the intensity of illumination on the surface of the sample was measured by using an illuminometer (Digital Lux Meter, FLX-1330, manufactured by Tokyo Gaishi Co.).

Several particles of the prepared paste-like curable composition of a size of a gain of rice were picked up on a white grinding paper to prepare samples. While being irradiated with light from the fluorescent lamp, the samples were crushed after every 10 seconds. A moment at which the interior of the sample started curing was regarded to be an operation margin time and was used as an indication of stability against environmental light.

(4) Handling Property of the Paste:

A suitable amount of the paste-like photocurable restorative prepared above was picked up in a suitable amount by using a dental filling device, and was heaped up on a gypsum model of an abutment tooth to prepare a restored tooth. The handing property of the paste in this case was evaluated on the basis of the following three stages.

Basis of Evaluation:

A: The paste exhibits a suitable viscosity without forming yarns, permitting easy heaping-up and easy modification of the shape.

B: The paste exhibits a slightly high or a slightly low viscosity, permitting heaping-up but without permitting the shape to be modified.

C: The paste cannot be heaped up.

(5) Measurement of the Mechanical Strength of the Cured Product:

The photocurable dental restorative prepared above was irradiated with light by using a visible light irradiator (α-Light manufactured by Morita Co.) for 5 minutes and was, then, polymerized at 100° C. for 15 minutes by using a heater/polymerizer (TP-1000 manufactured by Tokuyama Co.). The photocurable dental restorative was then immersed in water maintained at 37° C. for 24 hours and was, then, used as a sample piece.

(5-1) Bending Strength:

A square cylindrical sample piece measuring 2×2×25 mm was measured for its three-point bending breaking strength by using a tester (Autograph AG-5000D manufactured by Shimazu Seisakusho Co.) maintaining a distance of 20 mm between the fulcrums at a crosshead speed of 1 mm/min.

(5-2) Fracture Toughness:

A square pole-like test piece measuring 2 mm wide, 4 mm high and 20 mm long was formed, and was notched over a length of about 2 mm in the direction of height by using a cutter knife to prepare a three-point bending test piece having a notch on one side thereof. The sample piece was mounted on the tester (Autograph AG-5000D manufactured by Shimazu Seisakusho Co.) to carry out the three-point bending testing maintaining a distance of 16 mm between the fulcrums at a crosshead speed of 1 mm/min., and to calculate the fracture toughness from the fracture strength.

(6) Luster:

The surface of a test piece measuring 20 mm wide, 35 mm long and 1 mm thick was polished with a water-resistant polishing paper #1500 and was further polished with SOFLEX SUPERFINE (manufactured by 3M Co.). The surface of the test piece was then measured for its luster at a measuring angle of 45° by using an angle-variable lustermeter (TC-108D manufactured by Tokyo Denshoku Co.).

The luster is an index of surface glossiness. The luster 100 represents the total reflection. The luster which is close to 100 means that the surface glossiness is favorable.

(7) Coefficient of Thermal Expansion:

A test piece measuring 2 mm wide, 2 mm thick and 10 mm long was prepared and was measured for its dimensional change by using a heat mechanical analyzer (TMA120C manufactured by Rigaku Denki Co.) under the conditions of a temperature range of from −20 to 100° C., raising the temperature at a rate of 5° C./min and a load of 2.0 g, to calculate a coefficient of thermal expansion from 0 up to 60° C.

(8) Measurement of Unpolymerized Amount in the Surface:

A polyacetal mold having a hole of a size of 7 mm and a height of 1.5 mm was filled with the paste of the restorative which was, then, irradiated with light for one minute by using a visible light irradiator (Power Light manufactured by Tokuyama Co.).

After the irradiation has been finished, the cured product was taken out from the mold and was weighed. Thereafter, the cured product was immersed in ethanol, washed with ultrasonic waves, dried, and was weighed again to find a reduction in the weight.

By presuming a reduction in the weight to be equal to a reduction in the volume, the thickness (1.5 mm) of the cured product was multiplied by the reduction in the weight to find a thickness of the unpolymerized layer in the surface, which was, then, regarded to be the unpolymerized amount in the surface.

The test was conducted by using three test pieces, and an average value thereof was found.

EXAMPLE 1

The spherical inorganic particles B-1 (60 g) and the fine inorganic particles C-1 (40 g) were introduced into pure water, and were dispersed therein with a treating pressure of 60 MPa by using an emulsifying/dispersing machine of the type of giving a shock under super-high pressure (Nanomizer NM-LA31 manufactured by Tokushu Kika Kogyo Co.). The surfaces were treated with a γ-methacryloxypropyltrimethoxysilane. Thereafter, the solvent was distilled off followed by drying to obtain mixed particles.

Figure 1:
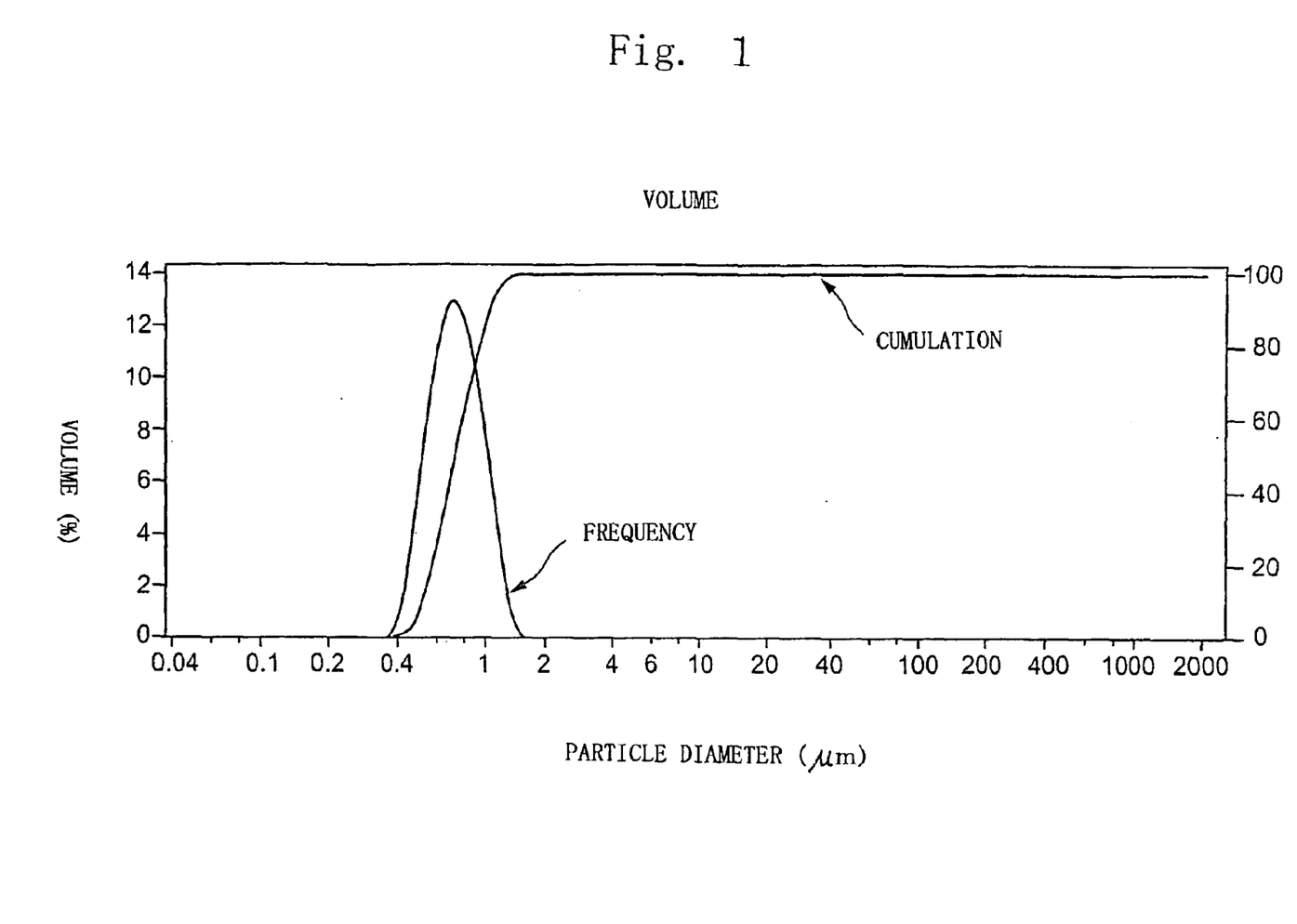
FIG. 1 is a diagram of particle size distribution curves of irregular-shaped inorganic particles A-1 used in Example 1.
Figure 2:
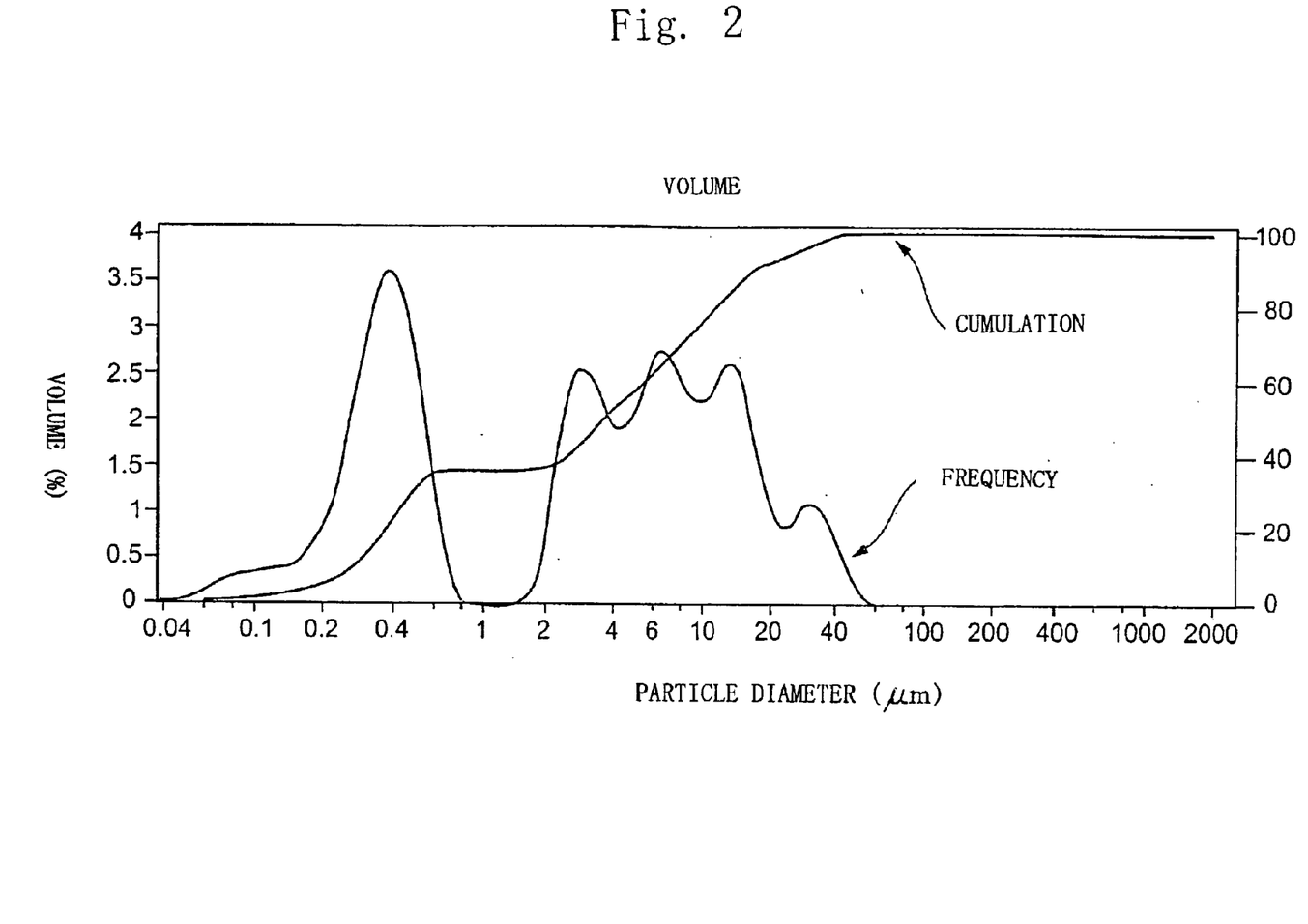
FIG. 2 is a diagram of particle size distribution curves of mixed particles of spherical inorganic particles B-1 and fine inorganic particles C-1 prepared in Example 1.

FIG. 1 illustrates a particle size distribution curve of the irregular-shaped inorganic particles A-1, and FIG. 2 illustrates a particle size distribution curve of the mixed particles of the spherical inorganic particles B-1 and of the fine inorganic particles C-1 prepared above. The particle size distribution is measured by using LS230 manufactured by Beckman Coulter Co., the portions in excess of 1 μm being measured by the laser diffraction method, and the portions not larger than 1 μm being measured by the light scattering method.

The above mixed particles and the irregular-shaped inorganic particles A-1 were introduced into a mortar at a following mass ratio:

$$mA\text{-}1/(mB\text{-}1+mC\text{-}1)=1.0$$

where mA-1 is a mass of A-1, mB-1 is a mass of B-1, and mC-1 is a mass of C-1, and were mixed and dispersed to obtain a mixed filler.

As a result of measuring the pore distribution of the mixed fillers, the volume of the micro pores due to strongly aggregated particles having pore sizes of not smaller than 0.08 μm was 0.04 cc/g.

As the polymerizable monomer (i), there were used D2.6E (70 parts by weight), 3G (15 parts by weight) and UDMA (15 parts by weight), and to which was added BAPO (0.5 parts by weight) as the polymerization initiator (ii) and was dissolved in a dark place to obtain a homogeneous solution thereof. To this solution (containing 100 parts by weight of the monomer) was added the mixed filler (400 parts by weight) prepared above to obtain a paste-like homogeneous curable composition (photocurable dental restorative).

Figure 3:
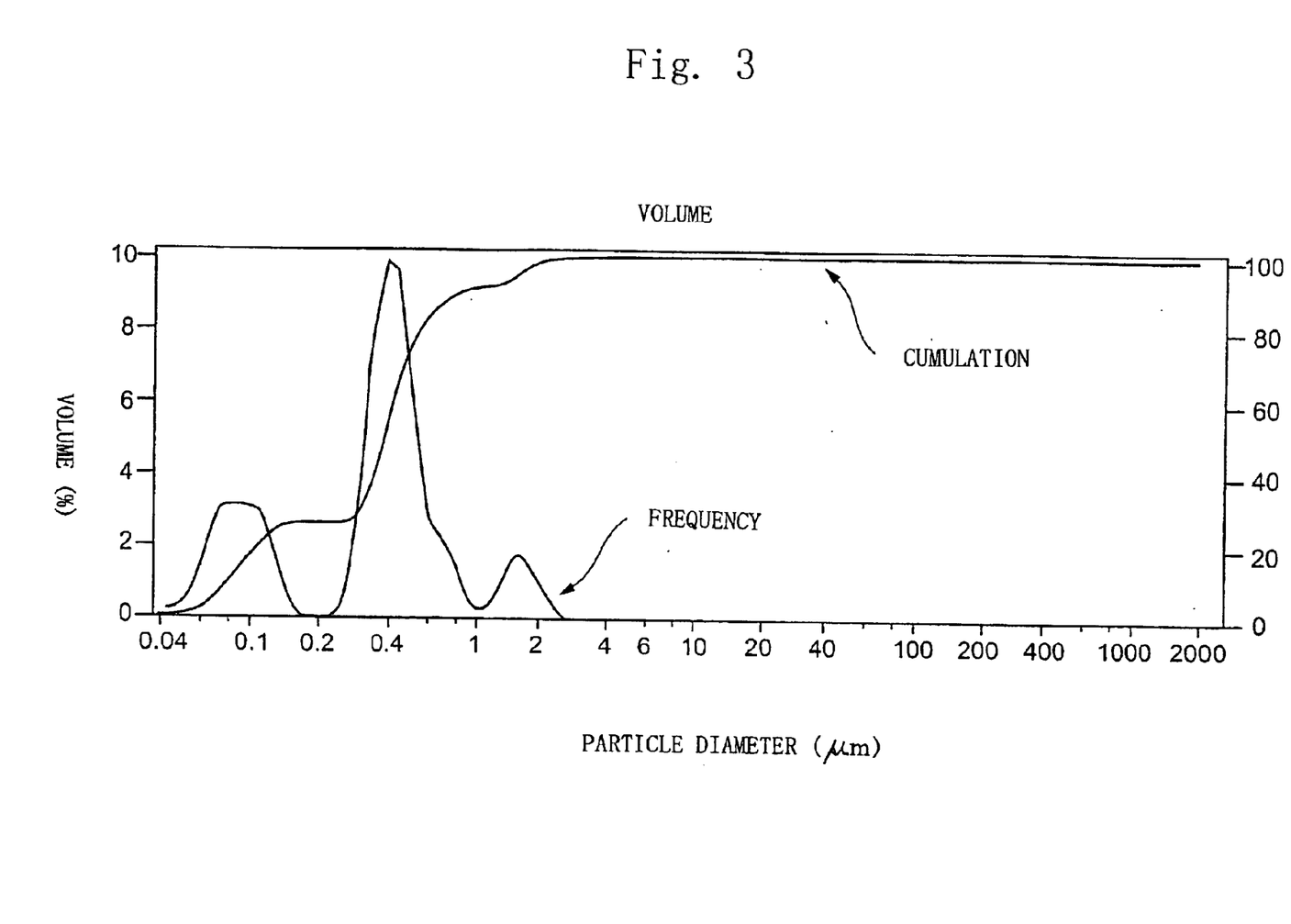
FIG. 3 is a diagram of particle size distribution curves of a mixed filler found by measuring the photocurable dental restorative (paste of a curable composition) prepared in Example 1 diluted with ethanol.

The curable composition was diluted with ethanol, and the particle size distribution of the mixed filler was measured relying upon the laser diffraction/light scattering method by using LS230 manufactured by Beckman Coulter Co. The results were as shown in FIG. 3. From the comparison of FIG. 2 with FIG. 3, it will be learned that the aggregates in the mixed filler are further disintegrated, and no peak is existing at positions in excess of 5 μm. It is further learned from the peaks of aggregates existing in a portion of from about 1 to about 3 μm that the total amount of the aggregates is not larger than 20% by volume.

The composition was measured for its stability against environmental light, handling property of the paste, bending strength of the cured product, fracture toughness, luster and coefficient of thermal expansion.

As a result, the stability against environmental light was 60 seconds, the bending strength was 246 MPa, the fracture toughness was 3.5 MPa·m$^{1/2}$, the luster was 80, and the coefficient of thermal expansion was 31.1 ppm/° C. The handling property of the paste was evaluated to be A.

EXAMPLES 2 TO 16

Pastes of curable compositions were prepared in the same manner as in Example 1 using the polymerizable monomer (i) which was quite the same as that of Example 1 but changing the curable compositions as shown in Table 1, and measurements were taken in the same manner. Table 2 shows the results thereof together with the results of Example 1.

In Examples 4, 5, 6, 9 and 16, an amine compound was blended in addition to the polymerizable monomer (i), photopolymerization initiator (ii) and mixed filler (iii).

In Table 1, the mixed fillers (iii) were prepared by blending the irregular-shaped inorganic particles (A), spherical inorganic particles (B) and fine inorganic particles (C) at ratios as represented by the following formulas:

Irregular-shaped inorganic particles (A): $RA=mA/(mB+mC)$

Spherical inorganic particles (B): $RB=mB/(mB+mC)$

Fine inorganic particles (C): $RC=mC/(mB+mC)$

EXAMPLE 17

The spherical inorganic particles B-1 (40 g) and the fine inorganic particles C-1 (60 g) were introduced into pure water, and were dispersed therein with a treating pressure of 60 MPa by using an emulsifying/dispersing machine of the type of giving a shock under super-high pressure. The surfaces were treated with the γ-methacryloxypropyltrimethoxysilane. Thereafter, the solvent was distilled off followed by drying to obtain surface-treated mixed particles.

40 Parts by weight of the above surface-treated mixed particles, 40 parts by weight of the irregular-shaped inorganic particles A-2 and 20 parts by weight of the spherical inorganic particles B-3 were introduced into a mortar, and were mixed and dispersed to obtain a mixed filler (iii).

By using the above mixed filler, a paste-like homogeneous curable composition (photocurable dental restorative) was prepared in the same manner as in Example 1 in compliance with the blended composition shown in Table 1.

The curable composition was measured in the same manner as in Example 1 to obtain results as shown in Table 2.

EXAMPLE 18

A paste-like homogeneous curable composition (photocurable dental restorative) was prepared in the same manner as in Example 1 but conducting the mixing and dispersion of the spherical inorganic particles B-1 and the fine inorganic particles C-1 by using a ball mill having a capacity of 2 liters for 2 hours instead of using the emulsifying/dispersing machine of the type of giving a shock under super-high pressure. Measurement was taken in the same manner as in Example 1 to obtain the results as shown in Table 2.

In all of the Examples as will be obvious from the experimental results of Table 2, the bending strength was not smaller than 210 MPa, the fracture toughness was not lower than 3.0 MPa·m$^{1/2}$ and luster was as favorable as about 80.

In Examples 14 to 17 using the 10-methacryloxydecyltrimethoxysilane as an agent for treating the surfaces of the irregular-shaped inorganic particles (A), further, it was possible to obtain the paste of the photocurable composition having a viscosity nearly comparable to that of Example 1 or 2 but being more highly densely filled with the inorganic filler than that of Examples 1 and 2 that used the γ-methacryloxypropyltrimethoxysilane. Therefore, the coefficient of thermal expansion of the obtained cured product of about 21 ppm/° C. was closer to the coefficients of thermal expansion (10 to 15 ppm/° C.) of the teeth.

Further, the filler was highly densely filled and, besides, a favorable handing property of the paste was accomplished when the volume of the micro pores due to the strongly aggregated particles of the mixed filler was not larger than 0.1, as will be obvious from the comparison of Example 1 or 2 in which the volume of the pores due to the strongly aggregated particles of the mixed filler was not larger than 0.1 with Example 18 in which the volume of the micro pores was not smaller than 0.1.

COMPARATIVE EXAMPLES 1 TO 14

Pastes of curable compositions were prepared in the same manner as in Example 1 but changing the curable compositions as shown in Table 1, and measurements were taken in the same manner. Table 2 shows the results thereof.

The spherical inorganic particles (B) and the fine inorganic particles (C) were those obtained by being dispersed under a treating pressure of 60 MPa by using the emulsifying/dispersing machine of the type of giving a shock under super-high pressure and by treating the surfaces thereof with the γ-methacryloxypropyltrimethoxysilane like in Example 1. In the curable compositions of Comparative Examples 5 and 9 to 12, the mixed filler was filled in a maximum amount with which the compositions still maintained a paste-like consistency.

In Comparative Examples 1 and 2, the irregular-shaped inorganic particles (A) were not used as the component of the mixed filler (iii) and in Comparative Examples 3 and 4, the irregular-shaped inorganic particles (A) were blended in small amounts (the mass ratio thereof was smaller than 0.2). In these cases, therefore, the fracture toughnesss were very lower than those of Examples.

In Comparative Example 5 blended with the irregular-shaped inorganic particles (A) in a large amount (the mass ratio thereof was not smaller than 3), the luster was poor, and the aesthetic appearance as the dental restorative was lacking. Besides, since the irregular-shaped inorganic particles (A) were blended at a ratio outside the scope of the present invention, the mixed filler was filled in an amount of 348 parts by weight at the greatest.

In Comparative Examples 6 and 7 using the inorganic particles A'-1 having an average particle size of 2.4 μm which lied outside the scope of the present invention as the irregular-shaped inorganic particles (A), the luster was very poor.

In Comparative Example 8, the fine inorganic particles (C) were blended at a ratio in excess of the range of the present invention. Therefore, both the fracture toughness and the bending strength were poor.

In Comparative Example 9 which was not blended with the spherical inorganic particles (B), both the fracture toughness and the bending strength were poor, and the luster was inferior, either.

In Comparative Examples 8 and 9, further, viscosities of the pastes were larger than those of the Examples though the fillers were filled at the same rate, and it was difficult to enhance the filling rate of the filler.

In Comparative Example 10, the fine inorganic particles (C) were not blended and in Comparative Example 11, the fine inorganic particles (C) were blended at a rate lower than the range specified by the present invention. In these cases, the fracture toughnesss were very low, and the bending strengths and lusters were low, either.

Comparative Examples 12 and 13 used no acylphosphine oxide as the photopolymerization initiator. In these cases, therefore, the fracture toughness were very low.

EXAMPLES 19 TO 25

Curable compositions of Examples shown in Table 3 were measured for their unpolymerized amounts in the surfaces.

As will be obvious from Table 3, in Examples 20, 21, 23 and 25 using the compositions blended with the amine compound, the unpolymerized amounts in the surfaces were smaller than those of other Examples which were not blended with the amine compound.

TABLE 1

| Example No. | Mixed inorganic filler composition | | | | | | Filler amount (weight parts) | Monomer composition (weight parts) | | | Photopolymerization initiator | | Amine compound | |
|---|---|---|---|---|---|---|---|---|---|---|---|---|---|---|
| | Irregular-shaped inorganic particle A | RA | Spherical inorganic particle B | RB | Fine inorganic particle C | RC | | D-2.6E | 3G | UDMA | Kind | Weight parts | Kind | Weight parts |
| Ex.1 | A-1 | 1.0 | B-1 | 0.6 | C-1 | 0.4 | 400 | 70 | 15 | 15 | BAPO | 0.5 | — | — |
| Ex.2 | A-1 | 1.0 | B-1 | 0.6 | C-1 | 0.4 | 400 | 70 | 15 | 15 | TPO | 0.5 | — | — |
| Ex.3 | A-1 | 0.3 | B-1 | 0.6 | C-1 | 0.4 | 450 | 70 | 15 | 15 | BAPO | 0.5 | — | — |
| Ex.4 | A-1 | 0.3 | B-1 | 0.6 | C-1 | 0.4 | 450 | 70 | 15 | 15 | BAPO | 0.5 | DMBE | 0.5 |
| Ex.5 | A-1 | 0.3 | B-1 | 0.6 | C-1 | 0.4 | 450 | 70 | 15 | 15 | TPO | 0.5 | DMBE | 0.5 |
| Ex.6 | A-1 | 0.3 | B-1 | 0.6 | C-1 | 0.4 | 400 | 70 | 15 | 15 | TPO | 0.5 | DMBE | 0.5 |
| Ex.7 | A-1 | 0.4 | B-1 | 0.6 | C-1 | 0.4 | 450 | 70 | 15 | 15 | BAPO | 0.5 | — | — |
| Ex.8 | A-1 | 0.7 | B-1 | 0.6 | C-1 | 0.4 | 450 | 70 | 15 | 15 | BAPO | 0.5 | — | — |
| Ex.9 | A-1 | 0.7 | B-1 | 0.6 | C-1 | 0.4 | 450 | 70 | 15 | 15 | BAPO | 0.5 | DMBE | 0.5 |
| Ex.10 | A-1 | 0.7 | B-1 | 0.6 | C-1 | 0.4 | 400 | 70 | 15 | 15 | BAPO | 0.5 | — | — |
| Ex.11 | A-1 | 2.3 | B-1 | 0.6 | C-1 | 0.4 | 380 | 70 | 15 | 15 | BAPO | 0.5 | — | — |
| Ex.12 | A-1 | 1.0 | B-1 | 0.7 | C-1 | 0.3 | 400 | 70 | 15 | 15 | BAPO | 0.5 | — | — |
| Ex.13 | A-1 | 1.0 | B-2 | 0.8 | C-2 | 0.2 | 400 | 70 | 15 | 15 | BAPO | 0.5 | — | — |
| Ex.14 | A-2 | 0.7 | B-1 | 0.6 | C-1 | 0.4 | 530 | 70 | 15 | 15 | BAPO | 0.5 | — | — |
| Ex.15 | A-2 | 0.7 | B-1 | 0.6 | C-1 | 0.4 | 530 | 70 | 15 | 15 | TPO | 0.5 | — | — |
| Ex.16 | A-2 | 0.7 | B-1 | 0.6 | C-1 | 0.4 | 530 | 70 | 15 | 15 | TPO | 0.5 | DMBE | 0.5 |
| Ex.17 | A-2 | 0.67 | B-1 B-3 | 0.27 0.33 | C-1 | 0.4 | 530 | 70 | 15 | 15 | BAPO | 0.5 | — | — |
| Ex.18 | A-1 | 1.0 | B-1 | 0.6 | C-1 | 0.4 | 380 | 70 | 15 | 15 | BAPO | 0.5 | — | — |
| Comp.Ex.1 | A-1 | 0.1 | B-1 | 0.6 | C-1 | 0.4 | 450 | 70 | 15 | 15 | BAPO | 0.5 | — | — |
| Comp.Ex.2 | A-1 | 0.1 | B-1 | 0.6 | C-1 | 0.4 | 400 | 70 | 15 | 15 | BAPO | 0.5 | — | — |
| Comp.Ex.3 | A-1 | 5.0 | B-1 | 0.6 | C-1 | 0.4 | 348 | 70 | 15 | 15 | BAPO | 0.5 | — | — |
| Comp.Ex.4 | — | — | B-1 | 0.6 | C-1 | 0.4 | 450 | 70 | 15 | 15 | BAPO | 0.5 | — | — |
| Comp.Ex.5 | — | — | B-1 | 0.6 | C-1 | 0.4 | 400 | 70 | 15 | 15 | BAPO | 0.5 | — | — |
| Comp.Ex.6 | A'-1 | 1.0 | B-1 | 0.6 | C-1 | 0.4 | 450 | 70 | 15 | 15 | BAPO | 0.5 | — | — |
| Comp.Ex.7 | A'-1 | 1.0 | B-1 | 0.6 | C-1 | 0.4 | 400 | 70 | 15 | 15 | BAPO | 0.5 | — | — |
| Comp.Ex.8 | A-1 | 1.0 | B-1 | 0.2 | C-1 | 0.8 | 246 | 70 | 15 | 15 | BAPO | 0.5 | — | — |
| Comp.Ex.9 | A-1 | 1.0 | — | — | C-1 | 1.0 | 207 | 70 | 15 | 15 | BAPO | 0.5 | — | — |
| Comp.Ex.10 | A-1 | 1.0 | B-1 | 1.0 | — | — | 353 | 70 | 15 | 15 | BAPO | 0.5 | — | — |
| Comp.Ex.11 | A-1 | 1.0 | B-1 | 0.997 | C-3 | 0.003 | 356 | 70 | 15 | 15 | BAPO | 0.5 | — | — |
| Comp.Ex.12 | A-1 | 1.0 | B-1 | 0.6 | C-1 | 0.4 | 400 | 70 | 15 | 15 | CQ | 0.5 | DMBE | 0.5 |
| Comp.Ex.13 | A-1 | 1.0 | B-1 | 0.6 | C-1 | 0.4 | 400 | 70 | 15 | 15 | CQ | 0.05 | DMBE | 0.5 |

TABLE 2

| Example No. | Pores volume due to aggregated (cc/g) | Stability to environmental light (sec) | Flexural strength (MPa) | Fracture toughness (MPa·m$^{1/2}$) | Luster | Coefficient of thermal expansion (ppm/°C.) | Handling of paste |
|---|---|---|---|---|---|---|---|
| Ex.1 | 0.04 | 60 | 246 | 3.5 | 80 | 31.1 | A |
| Ex.2 | 0.04 | 100 | 239 | 3.3 | 81 | 30.7 | A |
| Ex.3 | 0.02 | 60 | 225 | 3 | 83 | 29.8 | A |
| Ex.4 | 0.03 | 60 | 222 | 3.1 | 82 | 29.5 | A |
| Ex.5 | 0.02 | 110 | 226 | 3.1 | 81 | 30.2 | A |
| Ex.6 | 0.02 | 100 | 220 | 3.2 | 82 | 31.7 | A |
| Ex.7 | 0.02 | 60 | 232 | 3.2 | 82 | 28.5 | A |
| Ex.8 | 0.04 | 60 | 241 | 3.4 | 82 | 29.2 | B |
| Ex.9 | 0.04 | 60 | 244 | 3.3 | 81 | 29.7 | B |
| Ex.10 | 0.04 | 60 | 225 | 3.1 | 83 | 32.2 | A |
| Ex.11 | 0.03 | 60 | 218 | 3.3 | 78 | 33.3 | B |
| Ex.12 | 0.02 | 60 | 242 | 3.3 | 81 | 30.6 | A |
| Ex.13 | 0.02 | 60 | 220 | 3.4 | 82 | 31.5 | A |
| Ex.14 | 0.05 | 60 | 244 | 3.1 | 81 | 20.7 | A |
| Ex.15 | 0.05 | 100 | 240 | 3.3 | 79 | 21.2 | A |
| Ex.16 | 0.05 | 100 | 244 | 3.2 | 80 | 21.5 | A |
| Ex.17 | 0.06 | 60 | 239 | 3.1 | 80 | 21.2 | A |
| Ex.18 | 0.12 | 60 | 215 | 3.2 | 80 | 33.1 | B |
| Comp.Ex.1 | 0.02 | 60 | 229 | 2.1 | 84 | 29.3 | B |
| Comp.Ex.2 | 0.02 | 60 | 218 | 2.2 | 84 | 31.0 | A |
| Comp.Ex.3 | 0.04 | 60 | 235 | 2.7 | 61 | 34.1 | A |
| Comp.Ex.4 | 0.02 | 50 | 222 | 2.2 | 84 | 28.9 | A |
| Comp.Ex.5 | 0.02 | 60 | 215 | 2.1 | 84 | 31.7 | B |
| Comp.Ex.6 | 0.01 | 60 | 259 | 3.2 | 32 | 28.6 | A |
| Comp.Ex.7 | 0.01 | 60 | 233 | 3.3 | 37 | 31.1 | A |
| Comp.Ex.8 | 0.04 | 60 | 188 | 2.6 | 81 | 40.4 | B |
| Comp.Ex.9 | 0.04 | 60 | 195 | 2.7 | 69 | 42.8 | B |

TABLE 2-continued

| Example No. | Pores volume due to aggregated (cc/g) | Stability to environmental light (sec) | Flexural strength (MPa) | Fracture toughness (MPa · m½) | Luster | Coefficient of thermal expansion (ppm/° C.) | Handling of paste |
|---|---|---|---|---|---|---|---|
| Comp.Ex.10 | 0.03 | 60 | 202 | 2.3 | 76 | 35.2 | B |
| Comp.Ex.11 | 0.03 | 60 | 200 | 2.4 | 76 | 35.5 | B |
| Comp.Ex.12 | 0.04 | 20 | 231 | 2.2 | 80 | 29.8 | A |
| Comp.Ex.13 | 0.04 | 60 | 212 | 1.9 | 78 | 31.8 | A |

TABLE 3

| Example No. | Example No. of used composition | Amine compound blended | Unpolymerized amount in surface (μm) |
|---|---|---|---|
| 19 | 3 | no | 26 |
| 20 | 4 | yes | 18 |
| 21 | 5 | yes | 20 |
| 22 | 8 | no | 27 |
| 23 | 9 | yes | 20 |
| 24 | 10 | no | 29 |
| 25 | 16 | yes | 21 |

What is claimed is:

1. A photocurable dental restorative comprising (i) 100 parts by weight of a polymerizable monomer, (ii) 0.01 to 5 parts by weight of a photopolymerization initiator of acylphosphine oxide, and (iii) 200 to 1900 parts by weight of an inorganic filler, wherein the inorganic filler (iii) is a mixed filler of:

(A) irregular-shaped inorganic particles having an average particle size of not smaller than 0.1 μm but smaller than 1 μm;

(B) spherical inorganic particles having an average primary particle size of not smaller than 0.1 μm but not larger than 5 μm; and (C) fine inorganic particles having an average primary particle size of not larger than 0.1 μm;

which are so blended as to satisfy the following mass ratios ① to ③:

① mA/(mB+mC)=0.2 to 3
② mB/(mB+mC)=0.5 to 0.99
③ mC/(mB+mC) 0.01 to 0.5 where mA, mB and mC are masses of the inorganic particles (A) to (C).

2. A photocurable dental restorative according to claim 1, wherein said mixed filler (iii) is obtained by so blending the inorganic particles (A) to (C) as to satisfy the following mass ratios ①' to ③';

①' mA/(mB+mC)=0.4 to 2.3
②' mB/(mB+mC)=0.6 to 0.9
③' mC/(mB+mC)=0.1 to 0.4.

3. A photocurable dental restorative according to claim 1, wherein in said mixed filler (iii), a maximum size of aggregates of primary particles of the spherical inorganic particles (B) and a maximum size of aggregates of primary particles of the fine inorganic particles (C) are not larger than 20 μm, respectively, and a total amount of the aggregates thereof is not larger than 20% by volume of the whole mixed filler (iii).

4. A photocurable dental restorative according to claim 1, wherein said spherical inorganic particles (B) have an average primary particle size of not larger than 1 μm.

5. A photocurable dental restorative according to claim 1, wherein said fine inorganic particles (C) have an average primary particle size of from 0.05 to 0.09 μm.

6. A photocurable dental restorative according to claim 1, wherein said mixed filler (iii) has a volume of the pores of not smaller than 0.08 μm due to strongly aggregated particles of not larger than 0.1 cc/g.

7. A photocurable dental restorative according to claim 1, wherein said mixed filler (iii) has at least one distribution peak at a position of a particle size of not larger than 0.1 μm and at a position of a particle size of not smaller than 0.1 μm but not larger than 1 μm, respectively, on particle size distribution based on the volume of particles, but has no distribution peak at a position of a particle size in excess of 5 μm.

8. A photocurable dental restorative according to claim 1, wherein said acylphosphine oxide is represented by the following general formula (I) or (II)

(I)

(II)

wherein each of $R_1$, $R_2$, $R_3$, $R_4$ and $R_5$ is any one of the groups selected from the group consisting of a hydrogen atom, a halogen atom, an alkyl group, an alkoxy group, an alkylthio group, and an unsubstituted aryl group or a substituted aryl group substituted by at least one group selected from the group consisting of a halogen atom, an alkyl group and an alkoxy group, and each of $R_6$ and $R_7$ is any one of the groups selected from the group consisting of a substituted alkyl group or a substituted alkyl group substituted by at least one group selected from the group consisting of
a halogen atom,
an alkyl group and
an alkoxy group, a substituted alkenyl group or a substituted alkenyl group substituted by at least one group selected from the group consisting of
a halogen atom,
an alkyl group and
an alkoxy group, and an unsubstituted aryl group or a substituted aryl group substituted by at least one group selected from the group consisting of
a halogen atom,
an alkyl group and
an alkoxy group.

9. A photocurable dental restorative according to claim 1, wherein said irregular-shaped inorganic particles (A) are treated for their surfaces with a silane coupling agent represented by the following general formula (III), (III)

wherein $R_8$ is a hydrogen atom or a methyl group, $R_9$ is an alkoxy group, a chlorine atom or an isocyanate group, $R_{10}$ is an alkyl group having 1 to 6 carbon atoms, m is an integer of 2 to 3, and n is an integer of 8 to 20, and said fine inorganic particles (C) are treated for their surfaces with a silane coupling agent represented by the following general formula (IV), (IV)

wherein $R_{11}$ is a hydrogen atom or a methyl group, $R_{12}$ is an alkoxy group, a chlorine atom or an isocyanate group, $R_{13}$ is an alkyl group having 1 to 6 carbon atoms, m is an integer of 2 to 3, and n is an integer of 2 to 3.

10. A photocurable dental restorative according to claim 1, wherein an amine compound is contained in an amount of from 0.01 to 5 parts by weight per 100 parts by weight of the polymerizable monomer (i).

11. A method of producing a photocurable dental restorative by preparing an inorganic filler by mixing:
(A) irregular-shaped inorganic particles having an average particle size of not smaller than 0.1 μm but smaller than 1 μm;
(B) spherical inorganic particles having an average primary particle size of not smaller than 0.1 μm but not larger than 5 μm; and
(C) fine inorganic particles having an average primary particle size of not larger than 0.1 μm;
so as to satisfy the following mass ratios ① to ③:
① mA/(mB+mC)=0.2 to 3
② mB/(mB+mC)=0.5 to 0.99
③ mC/(mB+mC)=0.01 to 0.5
where mA, mB and mC are masses of the inorganic particles (A) to (C),
and by mixing 100 parts by weight of a polymerizable monomer, 0.01 to 5 parts by weight of a photopolymerization initiator of acylphosphine oxide, and 200 to 1900 parts by weight of said inorganic filler.

* * * * *